US010588834B2

(12) United States Patent
Swoboda

(10) Patent No.: US 10,588,834 B2
(45) Date of Patent: Mar. 17, 2020

(54) BIOSOURCED EMOLLIENT COMPOSITION COMPRISING ISOPARAFFINS

(71) Applicant: TOTAL MARKETING SERVICES, Puteaux (FR)

(72) Inventor: Benjamin Swoboda, Orgeval (FR)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

(21) Appl. No.: 15/759,655

(22) PCT Filed: Sep. 14, 2016

(86) PCT No.: PCT/EP2016/071718
§ 371 (c)(1),
(2) Date: Mar. 13, 2018

(87) PCT Pub. No.: WO2017/046177
PCT Pub. Date: Mar. 23, 2017

(65) Prior Publication Data
US 2019/0060192 A1    Feb. 28, 2019

(30) Foreign Application Priority Data
Sep. 16, 2015   (EP) .................................... 15185565

(51) Int. Cl.
*A61K 8/31*     (2006.01)
*A61Q 19/00*    (2006.01)
*A61K 8/06*     (2006.01)
*A61K 9/00*     (2006.01)
*A61K 47/44*    (2017.01)
*A61K 9/107*    (2006.01)

(52) U.S. Cl.
CPC ............... *A61K 8/31* (2013.01); *A61K 8/062* (2013.01); *A61K 9/0014* (2013.01); *A61K 9/107* (2013.01); *A61K 47/44* (2013.01); *A61Q 19/00* (2013.01); *A61K 2800/31* (2013.01); *A61K 2800/43* (2013.01); *A61K 2800/48* (2013.01); *C10G 2300/1014* (2013.01)

(58) Field of Classification Search
None
See application file for complete search history.

(56) References Cited

U.S. PATENT DOCUMENTS

| 3,439,088 A | 4/1969 | Edman |
| 3,818,105 A | 6/1974 | Coopersmith et al. |
| 4,724,139 A | 2/1988 | Palinczar |
| 6,428,775 B1 | 8/2002 | Habif et al. |
| 6,696,049 B2 * | 2/2004 | Vatter .................... A61K 8/345 424/401 |
| 2004/0230085 A1 | 11/2004 | Jakkula et al. |
| 2007/0189989 A1 | 8/2007 | Cantwell et al. |
| 2008/0193404 A1 | 8/2008 | Lange et al. |
| 2009/0014354 A1 | 1/2009 | Knuuttila et al. |
| 2009/0300970 A1 | 12/2009 | Perego et al. |
| 2015/0191404 A1 * | 7/2015 | Aalto ........................ C07C 1/22 585/16 |

FOREIGN PATENT DOCUMENTS

| DE | 10 2005 020 707 A1 | 11/2006 |
| DE | 10 2011 087 976 A1 | 8/2012 |
| DE | 10 2011 087 972 A1 | 6/2013 |
| EP | 2 368 967 A1 | 9/2011 |
| EP | 2 368 968 A1 | 9/2011 |
| WO | WO 2010/098126 A1 | 9/2010 |

OTHER PUBLICATIONS

Merriam-Webster definition Isoparaffin, accessed Jan. 9, 2019. (Year: 2019).*
International Search Report (PCT/ISA/210) issued in PCT/EP2016/071718, dated Oct. 26, 2016.
Hunter et al., "Analysis of Cold-Pressed Orange Oil Paraffin Waxes", Phytochemistry, 1966, vol. 5, pp. 807-809.
Nikitakis et al., "C10-40 Isoalkyl Acid Phytosterol Esters", International Cosmetic Ingredient Dictionary and Handbook, 2014, pp. 770-773, 1703, 4186, 4188.
Total, "Fluids and Solutions, Isoparaffins, Isane", http://www.total.de/shared/ccurl/179/11/ISANE_2011 .pdf, XP-002750636, Feb. 2, 2011, pp. 1-2.

* cited by examiner

*Primary Examiner* — Robert A Wax
*Assistant Examiner* — Melissa S Mercier
(74) *Attorney, Agent, or Firm* — Birch, Stewart, Kolasch & Birch, LLP

(57) ABSTRACT

Emollient composition comprising at least one hydrocarbon oil having an isoparaffin content of 90 to 100% by weight, a normal paraffin content of 0 to 10% by weight and a content of carbon of biological origin greater than or equal to 90% with respect to the total weight of hydrocarbon oil.

21 Claims, No Drawings

BIOSOURCED EMOLLIENT COMPOSITION COMPRISING ISOPARAFFINS

FIELD OF THE INVENTION

The invention relates to an emollient composition comprising at least one biodegradable hydrocarbon oil, of biological origin and mostly isoparaffinic.

The invention also relates to a cosmetic, dermatological or pharmaceutical composition comprising said emollient composition and the use thereof.

This invention also relates to the use of said emollient composition for the formulation of cosmetic products, of dermatological products or of pharmaceutical products.

TECHNICAL CONTEXT OF THE INVENTION

The cosmetics, dermatology or pharmacy markets are increasingly requesting ingredients of biological origin for the formulation of their products. Although biosourced active ingredients, emulsifiers and plant oils have developed substantially in the last few years and are now widely available in the market, biosourced emollients, especially hydrocarbon emollients with a 100% biological origin, are still rare.

The emollients currently used in cosmetics are either isoparaffins coming from petrochemicals (mainly isododecane and isohexadecane), white oils, silicone oils or oils with an ester base (synthetic or natural). The isoparaffins, white oils and silicone oils are widely distributed as they are very stable and odourless but do not come from renewable resources. Although volatile silicones such as cyclomethicone have for a long time been considered as harmless emollients and solvents for the skin (International Journal of Toxicology, Vol. 10, no. 1, pp. 9-19, 1991), fears have been expressed over the last few years concerning their potential harmful effects on the environment, and even on human health (in particular concerning octamethylcyclotetrasiloxane). Oils with an ester base in certain cases come from renewable resources but are not very stable and have a strong odour due to their unsaturated chemical structure.

To date, when the industries want to formulate products that comprise emollients comprising an "organic" connotation, they generally turn to synthetic emollients with an ester base, to plant oils or to so-called pure substances. U.S. Patent application 2007260102 describes for example a method of hydrotreatment of a plant oil and of a mineral oil in order to obtain a solvent comprising more than 98% of normal paraffins that can be used in cosmetic compositions. In the same way patent application WO2011146837 describes a method for preparing pure compounds that can be used in cosmetics, squalane and isosqualane, from the hydrogenation of β-farnesene. Patent application FR294428 describes an oily volatile composition used in cosmetics, for the replacement of silicone oils and isoparaffins, comprised of linear paraffins and obtained by dehydration of fatty alcohols of plant origin. These types of emollients have disadvantages that limit the application and the development thereof. These disadvantages are for example the instability with poor ageing properties, a pronounced odour that is hardly acceptable and/or a high price.

Therefore there is still a need to have a biosourced emollient composition that has physical-chemical and sensory characteristics in particular in terms of stability, volatility, spreading on the skin, odour, soft touch and brilliance, making it highly compatible with a use in formulation.

The applicant has surprisingly found that this need can be satisfied by a new emollient composition of biological origin comprising mostly isoparaffins and making it possible to carry out stable compositions with improved physical-chemical and sensory properties.

This invention has for objective to provide an isoparaffinic emollient composition coming from a raw material of biological origin.

This invention has for objective to provide an emollient composition with improved physical-chemical and sensory properties.

This invention also has for objective to propose a stable emollient composition with properties suitable for the use thereof.

SUMMARY OF THE INVENTION

These objectives are achieved thanks to a new emollient composition.

The invention relates to an emollient composition comprising at least one hydrocarbon oil having an isoparaffin content by weight of 90 to 100%, a normal paraffin content by weight of 0 to 10% and a content of carbon of biological origin greater than or equal to 90% with respect to the total weight of hydrocarbon oil.

Preferably, the hydrocarbon oil of the emollient composition of the invention comprises a content of carbon of biological origin greater than or equal to 95%, preferably greater than or equal to 98% and preferably of 100% with respect to the total weight of hydrocarbon oil.

Preferably, the hydrocarbon oil of the emollient composition of the invention has an isoparaffin content by weight of 90 to 100%, preferably of 95 to 100% and more preferably of 98% to 100% with respect to the total weight of hydrocarbon oil.

Preferably, the hydrocarbon oil of the emollient composition of the invention is chosen from non-cyclical isoparaffins comprising 14 to 18 carbon atoms.

Preferably, the hydrocarbon oil of the emollient composition of the invention comprises a content by weight of normal paraffins less than or equal to 10%, preferably less than or equal to 5% and more preferably less than or equal to 2% with respect to the total weight of hydrocarbon oil.

Preferably, the hydrocarbon oil of the emollient composition of the invention comprises a content by weight of naphthenic compounds less than or equal to 1%, preferably less than or equal to 0.5% and more preferably less than or equal to 100 ppm with respect to the total weight of hydrocarbon oil.

Preferably, the hydrocarbon oil of the emollient composition of the invention comprises a content by weight of aromatic compounds less than or equal to 500 ppm, preferably less than or equal to 300 ppm and more preferably less than or equal to 100 ppm with respect to the total weight of hydrocarbon oil.

Preferably, the hydrocarbon oil of the emollient composition of the invention has a boiling temperature of 230 to 340° C., preferably of 235 to 330° C. and more preferably of 240 to 325° C. according to the standard ASTM D86.

Preferably, the hydrocarbon oil of the emollient composition of the invention is obtained by a catalytic hydrogenation method at a temperature of 80 to 180° C. and at a pressure from 50 to 160 bars of a deoxygenated and/or isomerised load of biological origin.

Advantageously, the hydrocarbon oil of the emollient composition of the invention has a biodegradability at 28 days of at least 60%, preferably of at least 70%, more preferably of at least 75% and even more preferably of at least 80% measured according to standard OECD 306.

Preferably, the hydrocarbon oil of the emollient composition of the invention has a flash point greater than or equal to 110° C. according to the standard ASTM D93.

Preferably, the hydrocarbon oil of the emollient composition of the invention has a vapour pressure at 20° C. less than or equal to 0.01 kPa.

The invention also has for object a cosmetic, dermatological or pharmaceutical composition comprising at least one emollient composition of the invention, preferably in a quantity of 0.5 to 80%, preferably of 1 to 50% and advantageously of 5 to 30% by weight with respect to the total weight of the composition, preferably an emollient composition comprising 100% of hydrocarbon oil.

According to an embodiment the cosmetic, dermatological or pharmaceutical composition of the invention comprising at least one fatty body chosen from: plant oils, hydrocarbon oils other than the hydrocarbon oil of said emollient composition, plant butters, the fatty ethers and alcohols, oily esters, alkanes and silicone oils and/or at least one additive.

Another object of the invention is the cosmetic use of the emollient composition of the invention or of the cosmetic, dermatological or pharmaceutical composition of the invention for a topical application, in particular as a skin care product, as a makeup product, as a hair care product, as a makeup removal product, as a scented product, as a sunscreen product.

An object of the invention is also a pharmaceutical use of the emollient composition of the invention or of the cosmetic, dermatological or pharmaceutical composition of the invention.

Another object of the invention is also the use of the emollient composition of the invention or of the cosmetic, dermatological or pharmaceutical composition of the invention for the formulation of cosmetic products, of dermatological products or of pharmaceutical products.

The invention also has for object a method of cosmetic treatment of the skin comprising at least one step of application, preferably by spreading, of the emollient composition of the invention or of the cosmetic, dermatological or pharmaceutical composition of the invention.

DETAILED DESCRIPTION OF THE INVENTION

The invention relates to an emollient composition comprising at least one hydrocarbon oil having an isoparaffin content by weight of 90 to 100%, a normal paraffin content by weight of 0 to 10% and a content of carbon of biological origin greater than 95% with respect to the total weight of hydrocarbon oil.

The emollient composition according to the invention makes it possible to have a non-irritant, non-odorant and biodegradable composition.

The emollient composition according to the invention makes it possible in particular to obtain stable cosmetic, dermatological or pharmaceutical compositions.

The emollient composition according to the invention moreover has an emollient nature and an easy spreading on the skin in such a way that the formulated cosmetic, dermatological or pharmaceutical compositions leave on the skin, after penetration into the external layers thereof, a film having a soft and non-greasy touch.

On a preliminary basis note that, in the description and the following claims, the expression "between" must be understood as including the boundaries mentioned.

Emollient Composition:

The emollient composition according to the invention comprises more preferably a hydrocarbon oil content of 50 to 100% by weight, preferably of 80 to 100% by weight, more preferably of 90 to 100% by weight and advantageously equal to 100% by weight with respect to the total weight of the composition.

The presence of a significant quantity of hydrocarbon oil according to the invention contributes to the cosmetic, pharmaceutical and/or dermatological qualities of the emollient composition: pleasant touch, care, brilliance and protection of the skin.

The hydrocarbon oil of the emollient composition according to the invention preferably has a content by weight of isoparaffinic compounds greater than or equal to 90%, preferably greater than or equal to 95% and advantageously greater than or equal to 98% with respect to the total weight of hydrocarbon oil.

The hydrocarbon oil of the emollient composition according to the invention preferably has a content by weight of normal paraffins less than or equal to 10%, preferably less than or equal to 5% and advantageously less than or equal to 2%.

The hydrocarbon oil of the emollient composition according to the invention advantageously comprises a majority of isoparaffins and a minority of normal paraffins. These isoparaffins are advantageously non-cyclical isoparaffins. Preferably the hydrocarbon oil of the emollient composition has a ratio of isoparaffins over normal paraffins of at least 12:1, preferably of 15:1 and more preferably of 20:1. More advantageously the hydrocarbon oil of the emollient composition according to the invention does not contain any normal paraffins.

According to an embodiment, the hydrocarbon oil according to the invention comprises more preferably an isoparaffin content by weight of 90 to 100% and a normal paraffin content of 0 to 10%, preferably of 95 to 100% of isoparaffins and of 0 to 5% of normal paraffins and more preferably of 98% to 100% of isoparaffins and of 0 to 2% of normal paraffins.

The hydrocarbon oil of the emollient composition according to the invention comprises more preferably a content by weight of naphthenic compounds less than or equal to 1%, preferably less than or equal to 0.5% and more preferably less than or equal to 100 ppm.

According to another preferred embodiment, the hydrocarbon oil of the emollient composition according to the invention has an isoparaffin content by weight of 90 to 100%, a normal paraffin content by weight of 0 to 10% and a content by weight of naphthenes less than or equal to 1%. Preferably the hydrocarbon oil has a content by weight of 95 to 100% of isoparaffins, of 0 to 5% of normal paraffins and a content by weight of naphthenes less than or equal to 0.5%. More preferably it has a content by weight of 98% to 100% of isoparaffins, of 0 to 2% of normal paraffins and a content by weight of naphthenes less than or equal to 100 ppm.

The hydrocarbon oil implemented in the emollient composition according to the invention is advantageously free from aromatic compounds. The term free means a content by weight of aromatic compounds less than or equal to 500 ppm, preferably less than or equal to 300 ppm, preferably less than or equal to 100 ppm, more preferably less than or equal to 50 ppm and advantageously less than or equal to 20 ppm measured by UV spectrometry.

According to another preferred embodiment, the hydrocarbon oil of the emollient composition according to the invention has an isoparaffin content by weight of 90 to 100%, a normal paraffin content by weight of 0 to 10%, a content by weight of naphthenes less than or equal to 1% and a content by weight of aromatic compounds less than or equal to 500 ppm. Preferably the hydrocarbon oil has a content by weight of 95 to 100% of isoparaffins, of 0 to 5% of normal paraffins, a content by weight of naphthenes less than or equal to 0.5% and a content by weight of aromatic compounds less than or equal to 300 ppm, preferably less than 100 ppm. Preferably also the hydrocarbon oil has a content by weight of 95 to 100% of isoparaffins, of 0 to 5% of normal paraffins and a content by weight of aromatic compounds less than or equal to 100 ppm. More preferably it has a content by weight of 98% to 100% of isoparaffins, of 0 to 2% of normal paraffins, a content by weight of naphthenes less than or equal to 100 ppm and a content by weight of aromatic compounds less than or equal to 100 ppm.

The hydrocarbon oil implemented in the emollient composition according to the invention also preferably has an extremely low content by weight of sulphur compounds, typically less than or equal to 5 ppm, preferably less than or equal to 3 ppm and more preferably less than or equal to 0.5 ppm at a level that is too low to be detected using conventional low-sulphur content analysers.

The hydrocarbon oil implemented in the emollient composition according to the invention also preferably has a flash point greater than or equal to 110° C., preferably greater than or equal to 120° C. and more preferably greater than or equal to 140° C. according to the standard ASTM D93. A high flash point, typically greater than 110° C. making it possible among other things to overcome on the one hand the safety problems during the storage and transport by avoiding an excessively sensitive flammability of the hydrocarbon oil.

The hydrocarbon oil also preferably has a vapour pressure at 20° C. less than or equal to 0.01 kPa.

According to an embodiment, the hydrocarbon oil implemented in the emollient composition according to the invention also preferably has a flash point greater than or equal to 110° C. according to the standard ASTM D93 and a vapour pressure at 20° C. less than or equal to 0.01 kPa. Preferably the hydrocarbon oil has a flash point greater than or equal to 120° C. and a vapour pressure at 20° C. less than or equal to 0.01 kPa. And more preferably, it has a flash point greater than or equal to 140° C. and a vapour pressure at 20° C.

It was also discovered that when the paraffinic mixtures have a boiling temperature below 185° C., their flash point becomes too low, making them too dangerous as they are too sensitive to inflammation. It was also discovered that on the contrary when the boiling point of such mixtures exceeds 215° C., the volatile of the oil, defined by the vapour pressure, becomes too low rendering the emollient composition unpleasant for use as residues appear after application. The invention therefore offers a solution to the preceding problem.

The hydrocarbon oil implemented in the emollient composition according to the invention has boiling temperatures, a flash point and a vapour pressure that makes it possible to overcome the problems of flammability, odour and volatility.

The hydrocarbon oil of the emollient composition according to the invention furthermore has more preferably a kinematic viscosity at 40° C. less than or equal to 5 cSt, preferably less than or equal to 4 cSt and more preferably less than or equal to 4 cSt according to the standard ASTM D445.

Method of Obtaining:

Such hydrocarbon oil compositions can be obtained in the following way. The hydrocarbon oil according to the invention is a hydrocarbon fraction which comes from the conversion of the biomass.

The term coming from the conversion of the biomass means a hydrocarbon fraction produced using raw materials of biological origin.

Preferably, the hydrocarbon fraction of biological origin is obtained by a method comprising steps of hydrodeoxygenation (HDO) and of isomerisation (ISO). The step of hydrodeoxygenation (HDO) leads to the breakdown of the structures of biological esters or of the triglyceride constituents, to the elimination of oxygen, phosphorous and sulphur compounds and to the hydrogenation of the olefinic bonds. The product coming from the reaction of hydrodeoxygenation is then isomerised. A step of fractioning can more preferably follow the steps of hydrodeoxygenation and of isomerisation. Advantageously, the fractions of interest are then subjected to steps of hydrotreatment then distillation in order to obtain the specifications of the hydrocarbon oil sought according to the invention.

This HDO/ISO method is implemented over an untreated biological load, also called biomass or raw material of biological origin, selected from the group comprising plant oils, animal fats, fish oils and mixtures thereof. The suitable raw materials of biological origin are for example rapeseed oil, canola oil, tallol, sunflower oil, soybean oil, hemp oil, olive oil, linseed oil, mustard oil, palm oil, peanut oil, castor oil, coconut oil, animal fats such as tallow, recycle food fats, raw materials from genetic engineering, and biological raw materials produced using microorganisms such as algae and bacteria. Condensation products, esters or other derivatives obtained from untreated biological materials can also be used as raw materials.

Preferably, the raw material of biological origin is an ester or a triglyceride derivative. This material is subjected first of all to a step of hydrodeoxygenation (HDO) in order to break down the structure of the esters or constituent triglycerides and eliminate the oxygen, phosphorous and sulphur compounds concurrently to the hydrogenation of the olefinic bonds. This step of hydrodeoxygenation (HDO) of the raw material of biological origin is followed by an isomerisation of the product obtained as such leading to the branching of the hydrocarbon chain and to an improvement in the properties of the paraffin at low temperatures.

Durant the HDO step, hydrogen and the raw material of biological origin are passed over a catalytic bed of hydrodeoxygenation simultaneously or as a counter-current. Durant the HDO step, the pressure and the temperature are between 20 and 150 bars and between 200 and 500° C. respectively. Conventional and known catalysts of hydrodeoxygenation are used during this step. Optionally, the raw material of biological origin can be subjected to pre-hydrogenation under gentle conditions is order to avoid secondary reactions of the double bonds before the HDO step. After the step of hydrodeoxygenation, the product coming from the reaction is subjected to a step of isomerisation (ISO) where the hydrogen and the product, and optionally a mixture of n-paraffins, are passed over catalytic beds of isomerisation simultaneously or as a counter-current. During the ISO step, the pressure and the temperature are between 20 and 150 bars and between 200 and 500° C. respectively. Conventional and known catalysts of isomerisation are used during this step.

Additional secondary methods can also be implemented (such as intermediate mixtures, sequestrations or other methods of the sort).

The product coming from the HDO/ISO steps can possibly be fractioned in order to obtain the fractions of interest.

Various HDO/ISO methods are described in literature. Application WO2014/033762 describes a method comprising a step of pre-hydrogenation, a step of hydrodeoxygenation (HDO) and a step of isomerisation carried out against the current. Patent application EP1728844 describes a method of production of hydrocarbon compounds using a mixture of compounds of plant and animal origin. This method comprises a step of pre-treatment of the mixture making it possible to remove the contaminants, such as for example alkali metal salts, followed by a step of hydrodeoxygenation (HDO) and a step of isomerisation. Patent application EP2084245 describes a method of production of a hydrocarbon mixture that can be used as diesel fuel or in a composition of diesel fuel by hydrodeoxygenation of a mixture of biological origin containing fatty acid esters optionally in a mixture with free fatty acids, for example plant oils such as sunflower oil, rapeseed oil, canola oil, palm oil or pine oil, followed by a hydroisomerisation on specific catalysts. Patent application EP2368967 describes such a method and the product obtained by this method.

Advantageously, the raw material of biological origin contains less than 15 ppm of sulphur, more preferably less than 8 ppm, preferably less than 5 ppm and more preferably less than 1 ppm according to the standard EN ISO 20846. Ideally the load does not contain sulphur as a raw material of biosourced origin.

Before the step of hydrotreatment, a step of pre-fractioning can take place. A narrower fraction at the input of the hydrogenation unit makes it possible to obtain a narrow fraction at the output of the unit. Indeed, the boiling points of pre-fractionated fractions are between 220 and 330° C. while the fractions that were not pre-fractionated typically have boiling points between 150 and 360° C.

The deoxygenated and isomerised load coming from the HDO/ISO method is then hydrogenated.

The hydrogen used in the hydrogenation unit is typically highly purified hydrogen. The term highly purified means hydrogen with a purity for example greater than 99%, although other grades can also be used.

The step of hydrogenation is carried out using catalysts. The typical hydrogenation catalysts can be either bulk or supported and can include the following metals: nickel, platinum, palladium, rhenium, rhodium, nickel tungstate, nickel-molybdenum, molybdenum, cobalt-molybdenum. The supports can be silica, alumina, silica-alumina or zeolites.

A preferred catalyst is a catalyst with a nickel base on an alumina support of which the specific surface area varies between 100 and 200 m2/g of catalyst or a bulk catalyst with a nickel base. The conditions of hydrogenation are typically as follows:
Pressure: 50 to 160 bars, preferably 80 to 150 bars and more preferably 90 to 120 bars;
Temperature: 80 to 180° C., preferably 120 to 160° C. and more preferably 150 to 160° C.;
Hourly volume velocity (HVV): 0.2 to 5 hr$^{-1}$, preferably 0.4 to 3 hr$^{-1}$ and more preferably 0.5 to 0.8 hr$^{-1}$;
Rate of treatment by hydrogen: adapted to the conditions mentioned hereinabove and able to reach 200 Nm$^3$/tonnes of load to be treated.

The temperature in the reactors is typically between 150 and 160° C. with a pressure of about 100 bars while the hourly volume velocity is about 0.6 hr$^{-1}$ with a rate of treatment adapted according to the quality of the load to be treated and parameters of the first hydrogenation reactor.

The hydrogenation can take place in one or several reactors in series. The reactors can include one or several catalytic beds. The catalytic beds are generally fixed catalytic beds.

The method of hydrogenation comprises more preferably two or three reactors, preferably three reactors and is more preferably carried out in three reactors in series.

The first reactor allows for the sequestration of sulphur compounds and the hydrogenation of substantially all of the unsaturated compounds and up to about 90% of aromatic compounds. The product coming from the first reactor substantially contains no sulphur compound. In the second stage i.e. in the second reactor, the hydrogenation of the aromatics continues and up to 99% of the aromatics are therefore hydrogenated.

The third stage in the third reactor is a finishing stage that makes it possible to obtain contents in aromatics less than or equal to 500 ppm, preferably less than or equal to 300 ppm, preferably less than or equal to 100 ppm, more preferably less than or equal to 50 ppm, and ideally less than or equal to 20 ppm even in the case of products with a high boiling point for example greater than 300° C.

It is possible to use a reactor that comprises two or three catalytic beds or more. The catalysts can be present in variable or substantially equal quantities in each reactor; for three reactors, the quantities according to the weight can be for example 0.05-0.5/0.10-0.70/0.25-0.85, preferably 0.07-0.25/0.15-0.35/0.4-0.78 and more preferably 0.10-0.20/0.20-0.32/0.48-0.70.

It is also possible to use one or two hydrogenation reactors instead of three.

It is also possible for the first reactor to be comprised of twin reactors implemented alternatively. This operating mode allows in particular for an easy loading and unloading of the catalysts: when the first reactor comprises the catalyst that was saturated first (substantially all of the sulphur is sequestered on and/or in the catalyst) it has to be changed often.

A single reactor can also be used wherein two, three catalytic beds or more are installed.

It can be necessary to insert quench boxes into the recycle system or between the reactors in order to cool the effluents from one reactor to another or from one catalytic bed to another in order to control the temperatures and the hydrothermal balance of each reaction. According to a preferred embodiment, there are no cooling or quenching intermediaries.

According to an embodiment, the product coming from the method and/or the separated gases are at least partially recycled in the supply system of the hydrogenation reactors. This dilution contributes to maintaining the exothermicity of the reaction in the controlled limits, in particular in the first stage. The recycling furthermore allows for an exchange of heat before the reaction and also better control of the temperature.

The effluent of the hydrogenation unit mainly contains the hydrogenated product and hydrogen. Flash separators are used to separate the effluents into the gaseous phase, primarily the residual hydrogen, and into the liquid phase, mainly the hydrogenated hydrocarbon fractions. The method can be carried out by using three flash separators, one at a high pressure, one at an intermediate pressure and one at low pressure very close to atmospheric temperature.

The gaseous hydrogen which is collected at the top of the flash separators can be recycled in the supply system of the hydrogenation unit or at various levels in the hydrogenation units between the reactors.

According to an embodiment, the final product is separated at atmospheric temperature. It then directly supplies a vacuum fractionation unit. Preferably, the fractionating will be done at a pressure between 10 and 50 mbars and more preferably at about 30 mbars.

The fractionating can be carried out in such a way that it is possible to simultaneously remove various hydrocarbon fluids from the fractionating column and in that their boiling temperature can be predetermined.

By adapting the load through its initial and final boiling points, the hydrogenation reactors, the separators and the fractionation unit can therefore be directly connected without it being necessary to use intermediate tanks. This integration of the hydrogenation and of the fractionating allows for optimised thermal integration associated with a reduction in the number of apparatuses and energy savings.

The hydrocarbon oil implemented in the emollient composition of the invention is advantageously a hydrocarbon fraction that has a distillation range ID (in ° C.) of 230° C. to 340° C., preferably from 235° C. to 330° C. and more preferably of 240° C. to 325° C. measured according to the standard ASTM D86. Preferably, the difference between the initial boiling point and the final boiling point is less than or equal to 80° C., preferably less than or equal to 70° C., more preferably less than or equal to 60° C. and advantageously between 40 and 50° C. The hydrocarbon oil can include one or several fractions of distillation ranges included in the ranges described hereinabove.

Advantageously, the hydrocarbon oil implemented in the emollient composition of the invention is fully saturated. Preferably, the components of the hydrocarbon oil are chosen from isoparaffins comprising 13 to 27 carbon atoms, preferably 13 to 18 carbon atoms and more preferably 14 to 18 carbon atoms.

The emollient composition according to the invention advantageously comprises a content of isohexadecane less than or equal to 50%.

The hydrocarbon oil of the emollient composition according to the invention ideally comes from the treatment of raw materials of biological origin. The term "bio-carbon" indicates that the carbon is of natural origin and comes from a biomaterial, as indicated hereinafter. The content of bio-carbon and the content of biomaterial are expressions that indicate the same value. A material of renewable origin or biomaterial is an organic material wherein the carbon comes from the $CO_2$ recently fixed (on a human scale) by photosynthesis from the atmosphere. A biomaterial (Carbon 100% natural origin) has a $^{14}C/^{12}C$ isotopic ratio greater than $10^{-12}$, typically about $1.2 \times 10^{-12}$, while a fossil material has a zero ratio. Indeed, the isotopic $^{14}C$ is formed in and the atmosphere is then integrated by photosynthesis, according to a timescale of a few dozen years at most. The half-life of the $^{14}C$ is 5730 years. As such, the materials coming from the photosynthesis, namely plants generally, necessarily have a maximum content of isotope $^{14}C$.

The determination of the content of biomaterial or of bio-carbon is given in accordance with the standards ASTM D 6866-12, the method B (ASTM D 6866-06) and ASTM D 7026 (ASTM D 7026-04). The hydrocarbon oil of the emollient composition according to the invention has a content of biomaterial of at least 90%. This content is advantageously higher, in particular greater than or equal to 95%, preferably greater than or equal to 98% and advantageously equal to 100%.

In addition to a particularly high content of biomaterial, the hydrocarbon oil of the emollient composition according to the invention has a particularly good biodegradability. The biodegradation of an organic chemical product refers to the reduction in the complexity of the chemical compounds thanks to the metabolic activity of microorganisms. In aerobic conditions, the microorganisms transform the organic substances into carbon dioxide, water and biomass. The OCDE 306 method is used to evaluate the biodegradability of individual substances in sea water. According to this method, the hydrocarbon oil has a biodegradability at 28 days of at least 60%, preferably of at least 70%, more preferably of at least 75% and advantageously of at least 80%.

Miscibility of the Emollient Composition:

In addition to its improved physical-chemical and sensory properties due to the intrinsic composition of the hydrocarbon oil, the emollient composition according to the invention has a very good miscibility with the other fatty bodies conventionally used in the cosmetic, dermatological or pharmaceutical fields.

In particular, the emollient composition according to the invention has a good miscibility with the fatty bodies chosen in the group comprising: hydrocarbon oils of biological or petrochemical origin (other than the hydrocarbon oil of said emollient composition), plant oils, plant butters, fatty ethers and alcohols, oily esters, alkanes and silicone oils.

Hydrocarbon oils are fatty bodies coming from petrochemical methods. By way of example, mention can be made of mineral, oils, isoparaffins, waxes, paraffins, polyisobutenes or polydecenes.

Examples of plant oils are in particular the oils of wheat germ, sunflower, grape seed, sesame, corn, apricot, castor, shea, avocado, olive, soybean, the oil of sweet almond, palm, rapeseed, cotton, hazelnut, macadamia, jojoba, alfalfa, poppy, pumpkin, sesame, squash, rapeseed, blackcurrant, primrose, millet, barley, quinoa, rye, safflower, candlenut, passiflora, rose hip or camellia.

Plant butters are fatty bodies that have the same properties as plant oils. The difference between the two consists in the fact that the butters have a solid form at ambient temperature. Also, contrary to plant oils, the raw material of which a butter is extracted (pulp, grains or almonds) is heated after being crushed for the extraction of the fat. Like plant oils, butters can be refined in order to provide better preservation, neutralise odours, improve the colour and the consistency. Rich in antioxidants and nutrients the cosmetic properties of plant butters improve the elasticity of the skin, protect from exterior aggressions by leaving a protective film on the epidermis and as such reduce dehydration, repair and soothe by regenerating the natural hydrolipidic film of the skin. Examples of plant butters are in particular shea butter, cocoa butter, mango butter, shorea butter or olive butter.

Ethers and fatty alcohols are long-chain fatty waxy substances and have remarkable properties in particular they are film-forming, emollient, moisturising, softening and protective. They act as moisturising oils and as emulsifiers. Examples of fatty alcohol or ethers are: cetyl Alcohol, Stearyl Alcohol, myristyl alcohol, auryl alcohol, behenyl alcohol, cetearyl alcohol, dicaprylyl ethers, stearyl ethers or octyldodecanol (identified by their INCI name).

Oily esters or esterified oils are the product of a reaction between fatty acids (acids with longer chains, such as for example stearic acid, oleic acid, palmitic acid) and alcohols (of fatty alcohols or of polyols such as glycerol). These oils can contain substances coming from pertrochemistry, such as is the case for Isopropyl Palmitate. Examples of oily esters are caprylic capric triglyceride, coco caprylate caprate, oleyl erucate, oleyl linoleate, decyl oleate or PPG-3 benzyl ether myristate (identified by their INCI name).

The term silicone oils or polysiloxanes means an oil comprising at least one silicon atom, and in particular at least one Si—O group. As a silicone oil, mention can be made in particular of phenylpropyldimethylsiloxysilicate, dimethicones or cyclopentasiloxane (identified by their INCI name).

Additives:

The emollient composition according to the invention can also be placed in a mixture with any adjuvant or additive usually used in the fields considered and in particular in the cosmetic, dermatological or pharmaceutical fields. Of course, those skilled in the art will be sure to select the optional additive or additives of the composition according to the invention in such a way that the advantageous properties that are intrinsically attached to the emollient composition in accordance with the invention are not or are not substantially altered by the addition under consideration. Among the conventional adjuvants that are likely to be contained (according to the hydrosoluble or liposoluble nature of these adjuvants), mention can be made in particular of anionic foaming surfactants (such as sodium lauryl ether sulphate, sodium alkyl phosphate, trideceth sodium sulphate), amphoterics (such as alkyl betaine, disodium cocoamphodiacetate) or non-ionic with an HLB greater than 10 (such as POE/PPG/POE, Alkylpolyglucoside, polyglyceryl-3hydroxylauryl ether); preservatives; sequestrants (EDTA); antioxidants; perfumes; colouring agents such as soluble colouring agents, pigments and nacres; mattifying loads, tensors, whiteners or exfoliants; solar filters; cosmetic or dermatological active ingredients and agents that have the effect of improving the cosmetic properties of the skin, hydrophilic or lipophilic; electrolytes; hydrophilic or lipophilic polymers, anionic, non-ionic, cationic or amphoteric, thickeners, gelling agents or dispersants. The quantities of these various adjuvants are those conventionally used in the field considered, and for example of 0.01 to 20% of the total weight of the composition. As active ingredients that can be used in the emollient composition of the invention, mention can be made for example of hydrosoluble or liposoluble vitamins such as vitamin A (retinol), vitamin E (tocopherol), vitamin C (ascorbic acid), vitamin B5 (panthenol), vitamin B3 (niacinamide), the derivatives of these vitamins (in particular esters) and mixtures thereof; antiseptics; antibacterial active agents such as 2,4,4'-trichloro-2'-hydroxy diphenyl ether (or triclosan), 3,4,4'-trichlorocarbanilide (or triclocarban); antiseborrheic agents; antimicrobial agents such as benzoyl peroxide, niacin (vit. PP); slimming agents such as caffeine; optical brighteners, and any active agent that is suitable for the final purpose of the composition, and mixtures thereof.

This invention also has for object a cosmetic, dermatological or pharmaceutical composition comprising the emollient composition described hereinabove, at least one fatty body chosen from: plant oils, plant butters, fatty ethers and alcohols, oily esters, alkanes and silicone oils and at least one additive chosen from the aforementioned additives.

This cosmetic, dermatological or pharmaceutical composition comprises a physiologically acceptable medium, i.e. which does not have any harmful secondary effects and in particular which does not produce redness, heating, tugging or stinging that are inacceptable for a user. This medium optionally comprises water and/or at least one oil as a fatty body, in addition to the aforementioned emollient composition.

According to an embodiment the cosmetic, dermatological or pharmaceutical composition has a content of emollient composition such as described of 0.5 to 80%, preferably of 1 to 50% and advantageously of 5 to 30% by weight with respect to the total weight of the composition.

The cosmetic, dermatological or pharmaceutical composition according to the invention can as such be an anhydrous composition, an emulsion such as a water-in-oil emulsion (W/O), an oil-in-water emulsion (O/W) or a multiple emulsion (in particular W/O/W or O/W/O), a nano-emulsion, or a dispersion.

The cosmetic, dermatological or pharmaceutical composition according to the invention has the form of a more or less flexible cream or of a vaporisable emulsion, it can constitute for example a composition for makeup removal or cleaning of the skin, lips, a solar composition (U.V. protection), or after sunbathing, a composition for massaging the skin, a composition of shower care balm, an anti-perspirant composition, a mask composition, a repair balm composition, a smoothing and/or exfoliating composition for the face as well as for the hands (when it contains exfoliating particles), a makeup composition, a shaving composition, an after-shave balm composition, a perfumed composition, a composition for wipes or a vaporisable composition.

The composition of the invention is characterised advantageously by the fact that it has a stability with a duration greater than or equal to 4 weeks, advantageously greater than or equal to 6 weeks, with the stability being evaluated after a storage without stirring at ambient temperature, at 40° C. and at 50° C. and corresponding to a visual evaluation of the colouration and of the appearance as well as an olfactory evaluation and/or a measurement of the viscosity.

Use of the Emollient Composition:

The invention further has for object the cosmetic, dermatological or pharmaceutical use of the composition such as defined hereinabove for a topical application.

The invention also has for object the cosmetic, dermatological or pharmaceutical use of the composition such as defined hereinabove such as a skin care product (serums, creams, balms, etc.) as a hygiene product, as a sunscreen product/after sunbathing, as a makeup product, as a makeup removal product, as a scented product, as an anti-perspirant product.

The invention further has for object a cosmetic, dermatological or pharmaceutical method for treating the skin, comprising at least one step of application on the skin of a composition such as defined hereinabove.

The composition of the invention can also be used for the formulation of cosmetic compositions, dermatological compositions or pharmaceutical compositions comprising components or phases other than those described hereinabove. This can in particular be the formulation of care, hygiene, makeup compositions.

Method for Cosmetic Treatment:

Finally, the invention also covers a method of cosmetic treatment comprising at least one step of application, preferably by spreading, on the skin of the compositions according to the invention.

EXAMPLES

In the rest of this description, examples are given for the purposes of information of this invention and do not in any way intend to limit the scope of it.

Various biosourced emollient compositions according to the invention and an emollient composition that is conventionally found in the field of the invention were evaluated pure or in formulation. This evaluation covers both the sensory potential of these pure emollient compositions or in formulation as well as on their stability over time.

The various formulations evaluated are an oil-in-water emulsion and a dry oil comprising at least one emollient composition according to the invention.

Emollient Compositions:

Table 1 includes the physical-chemical properties of the various emollient compositions evaluated.

The compositions A, B and C are biosourced emollient compositions according to the invention. The composition D is a comparative emollient composition marketed by the company Croda under the commercial name Arlamol HD. This emollient composition is an isohexadecane coming from petrochemistry and conventionally found in the cosmetic market for example.

Evaluation of the Pure Emollient Compositions:

The pure emollient compositions are evaluated as sensory and organoleptic analysis. The evaluation criteria are as follows:

Bulk intrinsic odour: odour given until a homogeneous phase is obtained by the composition when the bottle is open (no application carried out).

Distribution on the skin: a drop is left on the skin for 30 seconds. After 30 seconds, the capacity of the drop to be distributed or spread without manual assistance is evaluated.

Spreading: does the composition have a resistance to movement when it is applied.

Brilliance on the skin: does a brilliant film persists on the skin once the composition is applied.

Crisp to the touch: once the composition is applied, is a persistent residue perceived between the fingers and if they are rubbed together, can a noise be heard.

Fatty: (criterion evaluated on the skin 1 minute after spreading) when the skin is placed between the thumb and the index, and a friction movement is carried out, is there any resistance. Does the composition facilitate the displacement of the two fingers while still giving the skin an oily appearance.

Penetration: (criterion evaluated on the skin 2 minutes after spreading) by carrying out a sliding on the skin, did the composition disappear and no residue was recovered.

Persistent odour on the skin: (criterion evaluated on the skin 2 minutes after spreading) After 2 minutes of application, can a lingering odour be perceived on the skin.

The sensory and organoleptic analysis is carried out by a panel of 5 people. The analysis is carried out on the underside of the forearm by depositing one or two drops of

TABLE 1

| Characteristics | Emollient composition A (according to the invention) | Emollient composition B (according to the invention) | Emollient composition C (according to the invention) | Emollient composition D (Comparative example—Arlamol HD) |
|---|---|---|---|---|
| Aromatics (ppm) | <20 | <20 | <20 | <1 |
| Sulphur (ppm) | 0.1 | 0.1 | 0.11 | |
| % iso paraffins (w/w) | 98.9 | 95.1 | 96.2 | >99 |
| % n-paraffins (w/w) | 1.1 | 4.9 | 3.8 | <1 |
| % naphthenics (w/w) | 0 | 0 | 0 | 0 |
| C13 (iso) | 0.66 | 0 | 0 | 0 |
| C14 (iso) | 4.15 | 0.12 | 0 | 0 |
| C15 (iso) | 48.35 | 11.45 | 0 | 0 |
| C16 (iso) | 42.80 | 47.89 | 1.58 | 100 |
| C17 (iso) | 2.52 | 18.57 | 14.17 | 0 |
| C18 (iso) | 0.38 | 17.07 | 79.69 | 0 |
| C19 (iso) | 0 | 0 | 0.12 | 0 |
| C20 (iso) | 0 | 0 | 0.38 | 0 |
| C27 (iso) | 0 | 0 | 0.29 | 0 |
| Quantity of carbons of biological origin (%) | 97 | 97 | 98 | 0 |
| Initial boiling point (° C.) | 247.0 | 259.5 | 293.6 | 210 |
| Boiling point 5% (° C.) | 255.7 | 270.2 | 296.7 | 230 |
| Boiling point 50% (° C.) | 258.9 | 274.5 | 298.5 | |
| Boiling point 95% (° C.) | 266.8 | 286.4 | 305.3 | 238 |
| Final boiling point (° C.) | 269.0 | 287.5 | 324.1 | 250 |
| OECD biodegradability (28 days) (%) | 80 | 83 | 83 | <60 |
| Refractive index at 20° C. | 1.4336 | 1.4357 | 1.4394 | 1.439 |
| density at 15° C. (kg/m3) | 776.4 | 780.3 | 787.2 | 790 |
| Flash point (° C.) | 115 | 125 | 149 | 102 |
| Kinematic Viscosity at 40° C. (cSt) | 2.49 | 2.94 | 3.87 | 4.2 |
| Vapour pressure at 20° C. (kPa) | <0.01 | <0.01 | <0.01 | 0.01 | each emollient composition using a glass pipette, the composition is then applied using the fingers. The number of drops applied can be reproduced for the same tester. 4 tests are carried out for each one of the compositions. A scoring system (from 0 to 5 from the least pronounced to the most pronounced) is set up in order to facilitate the operation.

Table 2 includes the averages of the scoring results obtained for each sensory criterion evaluated for the various emollient compositions; in this table on the characteristic of the odour, it is the lingering odour which is the most important characteristic.

TABLE 2

|  | Emollient composition A | Emollient composition B | Emollient composition C | Emollient composition D |
|---|---|---|---|---|
| mass intrinsic odour | 3.5 | 2.8 | 4.2 | 0.7 |
| distribution on the skin | 2.8 | 2.9 | 1.8 | 3.7 |
| spreading | 4 | 3.7 | 3.1 | 3.8 |
| brilliance on the skin | 3.1 | 1.7 | 2.2 | 2.5 |
| crisp to the touch | 1.4 | 1.6 | 1 | 1.7 |
| fat | 3.1 | 2.3 | 3 | 3 |
| penetration | 2.1 | 3.4 | 2.2 | 2.8 |
| lingering odour | 1.7 | 0.9 | 1.2 | 0.5 |

It is observed that the emollient compositions A, B and C have a sensory profile that is substantially comparable to that of the comparative emollient composition D.

Emollient Compositions in Formulation:
Oil-in-water Emulsion (O/W)

Conventional and non-perfumed oil-in-water emulsions (O/W) are formulated with each one of the exemplified emollient compositions.

The exemplified O/W emulsions include the various emollient compositions A, B, C and D in proportions of 0%, 5%, 10% and 15% by weight in relation to the total weight of the emulsion. As the total quantity of emollient remains constant at 15% in the formulations, the emollient compositions A, B and C are placed in a mixture with the comparative emollient composition D.

Three emulsions of 500 g are as such formulated with each one of the compositions A, B and C.

10 O/W emulsions are as such evaluated as a total (with the O/W emulsion number 10 comprising the comparative emollient composition D with a content of 15% being the comparative emulsion for each one of the formulations).

The formulation of the O/W emulsions is carried out using a Supertest and a turrax which make it possible to homogenise the emulsion by refining the size of the droplets.

The structure of the O/W emulsion evaluated remains the same for all of the tests. Only the quantities of the various emollient compositions of the fatty phase vary.

Table 3 hereinbelow indicates the formulations of the O/W emulsions according to the examples. The percentages indicated correspond to the weight in active material in relation to the total weight of the emulsion. For all of the emulsions, the base of the fatty phase is the same and the aqueous phase is identical in all of the cases.

TABLE 3

| Phases | | Commercial name | Emulsion 1 | Emulsion 2 | Emulsion 3 | Emulsion 4 | Emulsion 5 |
|---|---|---|---|---|---|---|---|
| FATTY PHASE | Phase A | Simulsol 165 (emulsifier) | 3.50% | 3.50% | 3.50% | 3.50% | 3.50% |
| | | Montanov 68 (emulsifier) | 1.50% | 1.50% | 1.50% | 1.50% | 1.50% |
| | | Lanette O OR (viscosity regulator) | 0.50% | 0.50% | 0.50% | 0.50% | 0.50% |
| | | Karité CP (fatty body) | 2.00% | 2.00% | 2.00% | 2.00% | 2.00% |
| | | Dub DSPE (viscosity agent) | 0.60% | 0.60% | 0.60% | 0.60% | 0.60% |
| | | Emollient composition A | 5.00% | 10.00% | 15.00% | — | — |
| | | Emollient composition B | — | — | — | 5.00% | 10.00% |
| | | Emollient composition C | — | — | — | — | — |
| | | Emollient composition D | 10.00% | 5.00% | 0.00% | 10.00% | 5.00% |
| AQUEOUS PHASE | Phase B | Demineralised water | 69.25% | 69.25% | 69.25% | 69.25% | 69.25% |
| | | Xanthan gum | 0.20% | 0.20% | 0.20% | 0.20% | 0.20% |
| | | Glycerine | 3.00% | 3.00% | 3.00% | 3.00% | 3.00% |
| | | Carbopol Ultrez 21 (polymer) | 0.20% | 0.20% | 0.20% | 0.20% | 0.20% |
| | Phase C | Phenoxethol (preservative) | 0.80% | 0.80% | 0.80% | 0.80% | 0.80% |
| | | Aqueous solution of NaOH at 10% | 0.30% | 0.30% | 0.30% | 0.30% | 0.30% |
| | Phase D | Demineralised water | 2.00% | 2.00% | 2.00% | 2.00% | 2.00% |
| | | Hydrolite-5 (stabiliser) | 1.00% | 1.00% | 1.00% | 1.00% | 1.00% |
| | | Chlorphenesin BP 73 (preservative) | 0.25% | 0.25% | 0.25% | 0.25% | 0.25% |

| Phases | | Commercial name | Emulsion 6 | Emulsion 7 | Emulsion 8 | Emulsion 9 | Emulsion 10 |
|---|---|---|---|---|---|---|---|
| FATTY PHASE | Phase A | Simulsol 165 (emulsifier) | 3.50% | 3.50% | 3.50% | 3.50% | 3.50% |
| | | Montanov 68 (emulsifier) | 1.50% | 1.50% | 1.50% | 1.50% | 1.50% |
| | | Lanette O OR (viscosity regulator) | 0.50% | 0.50% | 0.50% | 0.50% | 0.50% |
| | | Karite CP (fatty body) | 2.00% | 2.00% | 2.00% | 2.00% | 2.00% |

TABLE 3-continued

|  |  |  |  |  |  |  |  |
|---|---|---|---|---|---|---|---|
|  |  | Dub DSPE (viscosity agent) | 0.60% | 0.60% | 0.60% | 0.60% | 0.60% |
|  |  | Emollient composition A | — | — | — | — | 0.00% |
|  |  | Emollient composition B | 15.00% | — | — | — | — |
|  |  | Emollient composition C | — | 5.00% | 10.00% | 15.00% | — |
|  |  | Emollient composition D | 0.00% | 10.00% | 5.00% | 0.00% | 15.00% |
| AQUEOUS PHASE | Phase B | Demineralised water | 69.25% | 69.25% | 69.25% | 69.25% | 69.25% |
|  |  | Xanthan gum | 0.20% | 0.20% | 0.20% | 0.20% | 0.20% |
|  |  | Glycerine | 3.00% | 3.00% | 3.00% | 3.00% | 3.00% |
|  |  | Carbopol Ultrez 21 (polymer) | 0.20% | 0.20% | 0.20% | 0.20% | 0.20% |
|  | Phase C | Phenoxethol (preservative) | 0.80% | 0.80% | 0.80% | 0.80% | 0.80% |
|  |  | Aqueous solution of NaOH at 10% | 0.30% | 0.30% | 0.30% | 0.30% | 0.30% |
|  | Phase D | Demineralised water | 2.00% | 2.00% | 2.00% | 2.00% | 2.00% |
|  |  | Hydrolite-5 (stabiliser) | 1.00% | 1.00% | 1.00% | 1.00% | 1.00% |
|  |  | Chlorphenesin BP 73 (preservative) | 0.25% | 0.25% | 0.25% | 0.25% | 0.25% |

Preparation Mode:

The water of the phase B is weighed. Without agitation, the Carbopol Ultrez 21 is sprinkled into the water for hydration for 10 minutes without stirring. Then, the mixture is placed under stirring and heated to 50° C. At 50° C., a premix is carried out between the Rhodicare T and the glycerine then it is poured into the water under strong stirring. The agitation is maintained until a homogeneous phase is obtained. Finally the heating is continued to 75° C.

The phase A is weighed, placed under stirring and heated to 75° C.

At 75° C., under strong stirring (1150 rpm), the phase A is progressively poured into the phase B. The cooling is then initiated.

At 72° C. the emulsion put into the turrax 30 seconds at 9500 rpm.

The cooling is then continued to 50° C. under moderate stirring (500 rpm). At 50° C., under stirring, the components of the phase C are incorporated one by one into the emulsion. The cooling is continued to 30° C.

A 30° C., under stirring, the phase D (stirred beforehand until a homogeneous phase is obtained) is poured into the emulsion. The pH is adjusted if necessary (with a soda solution of 10%) between 5.50 and 6.00.

Evaluation of the Oil-in-water Emulsions (O/W):

Stability:

The stability study of the O/W emulsions is carried out at ambient temperature (TA) of the day, at 40° C. and at 50° C. for one month by visual and olfactory evaluation of the appearance, of the colour and of the odour as well as by evaluation of the viscosity of the emulsions over time.

No modification in the appearance or in the colour or any appearance of odour were observed during the visual and olfactory evaluation of the 10 oil-in-water emulsions formulated.

The viscosities are measured using the Brookfield RV DVII+PRO apparatus, mobile 6 to 20 revolutions per minute, for 1 minute in pots of 200 g have been temperature controlled beforehand between 24.5 and 25.5° C.

Table 4 indicates the results of the evaluation of the viscosity of the 10 O/W emulsions.

TABLE 4

|  |  | Emulsion 1 | Emulsion 2 | Emulsion 3 | Emulsion 4 | Emulsion 5 | Emulsion 6 | Emulsion 7 | Emulsion 8 | Emulsion 9 | Emulsion 10 |
|---|---|---|---|---|---|---|---|---|---|---|---|
| Viscosity (mPA · s) | D0 | 34,150 | 32,900 | 35,100 | 30,750 | 24,150 | 30,350 | 29,350 | 32,400 | 28,600 | 30,600 |
|  | D + 1 | 32,250 | 33,500 | 34,300 | 35,100 | 30,300 | 34,300 | 32,050 | 36,450 | 31,750 | 30,900 |
|  | 2 weeks | 34,550 | 36,150 | 41,050 | 35,300 | 30,450 | 34,950 | 32,400 | 37,150 | 33,350 | 34,950 |
|  | 4 weeks | 34,300 | 36,900 | 42,100 | 37,950 | 31,200 | 34,900 | 33,450 | 34,900 | 31,150 | 35,550 |
|  | 8 weeks | 37,500 | 38,000 | 43,200 | 35,700 | 31,650 | 34,250 | 34,050 | 37,450 | 35,100 | 35,950 |

A similar viscosity is observed for all of the O/W emulsions formulated. The viscosity of the emulsions remains stable over time. (A very slight general increase in the viscosity after 8 weeks is observed for all of the 10 O/W emulsions. It is considered to be insignificant as it is linked to the maturing of the emulsions).

Sensory Analysis:

The 10 O/W emulsions formulated are also evaluated in sensory analysis. The evaluation criteria are then adapted to the galenics and are as follows:

Bulk intrinsic odour: odour given until a homogeneous phase is obtained by the emulsion when the bottle is opened (no application carried out).

Spreading: does the emulsion have any resistance to the movement when it is applied.

Brilliance on the skin: does a brilliant film persist on the skin once the emulsion is applied.

Penetration speed: This entails evaluating if the penetration of the emulsion is faster or slower according to the sample. By carrying out a sliding on the skin, did the emulsion disappear and no residue is recovered.

Fatty (after penetration): is there a resistance when the skin is placed between the thumb and the index and a friction movement is carried out. Does the emulsion facilitate the displacement of the two fingers while still giving the skin an oily appearance.

Softness (after penetration): What is the softness felt when the palm of the hand is passed over the spreading zone of the emulsion. Is the skin softer over the spreading zone.

Tacky (after penetration): is an adherence of the skin felt when the palm of the hand is placed on the spreading zone of the emulsion, then removed. Is the skin more tacky.

Persistent odour on the skin (2 min): (criterion evaluated on the skin 2 minutes after spreading) After 2 minutes of application, can a lingering odour be perceived on the skin.

As for the sensory analysis of the pure emollient compositions, a scoring system (from 0 to 5 from the least pronounced to the most pronounced) is set up in order to facilitate the operation.

Table 5 includes the average scoring results for each one of the sensory criteria evaluated for the various O/W emulsions.

TABLE 5

|  | Emulsion 1 | Emulsion 2 | Emulsion 3 | Emulsion 4 | Emulsion 5 | Emulsion 6 | Emulsion 7 | Emulsion 8 | Emulsion 9 | Emulsion 10 |
|---|---|---|---|---|---|---|---|---|---|---|
| mass intrinsic odour | 1.7 | 1.4 | 1.6 | 1.2 | 1.2 | 1.2 | 1.7 | 1.8 | 1.7 | 1.8 |
| spreading | 2.7 | 3.7 | 3.1 | 2.7 | 2.6 | 2.9 | 2.7 | 3.1 | 3.2 | 2.2 |
| brilliance on the skin | 1.5 | 1.6 | 1.5 | 1.7 | 1.4 | 1.7 | 1.3 | 1.6 | 1.6 | 1.2 |
| penetration speed | 2.8 | 2.2 | 2.3 | 2.6 | 2.7 | 2.4 | 2.4 | 2.6 | 2.3 | 2.7 |
| fat | 1.8 | 2.1 | 1.9 | 1.7 | 1.2 | 1.5 | 2.1 | 1.7 | 2 | 1.4 |
| gentle | 2.2 | 2 | 2.5 | 2 | 2.7 | 2.5 | 2.5 | 2.5 | 2.2 | 2 |
| sticky | 0.8 | 0.9 | 1 | 0.3 | 0.8 | 1 | 1.1 | 0.9 | 1.4 | 1 |
| lingering odour | 1.7 | 1.6 | 1.75 | 1.3 | 1.4 | 1.5 | 1.6 | 1.5 | 1.6 | 1.8 |

It is observed that all of the emulsions comprising the emollient compositions A, B and C have a lingering odour and a less substantial intrinsic odour, a better spreading, a more substantial softness and a brilliance on the skin that is more pronounced than the emulsion 10 which comprises the comparative emollient composition D. These results with full formulated compositions have a remarkable improvement in relation to those obtained for the pure emollient compositions.

Galenic Anhydride (Dry Oils)

Dry oils for the body, not perfumed, containing 30% of emollient composition as a total are formulated with each one of the exemplified emollient compositions.

The oils for the body formulated include the various emollient compositions A, B and C in proportions of 10%, 20% and 30%. As the total quantity of emollient composition remains constant in the formulations, the emollient compositions A, B and C are placed in a mixture with the comparative composition D.

Three dry oils of 300 g are formulated with each one of the emollient compositions A, B and C.

10 dry oils for the body were thus evaluated as a total (with the dry oil number 10 comprising the comparative emollient composition D at a content of 30% being the comparative oil for each one of the formulations).

Table 6 hereinbelow indicates the formulations of the dry oils according to the examples. The percentages indicated correspond to the weight in active material in relation to the total weight of the composition.

TABLE 6

|  | Dry oil 1 | Dry oil 2 | Dry oil 3 | Dry oil 4 | Dry oil 5 | Dry oil 6 | Dry oil 7 | Dry oil 8 | Dry oil 9 | Dry oil 10 |
|---|---|---|---|---|---|---|---|---|---|---|
| Dub MCT 55/45 ester constituting the framework of the anhydrous formulation | 35.00% | 35.00% | 35.00% | 35.00% | 35.00% | 35.00% | 35.00% | 35.00% | 35.00% | 35.00% |

TABLE 6-continued

|  | Dry oil 1 | Dry oil 2 | Dry oil 3 | Dry oil 4 | Dry oil 5 | Dry oil 6 | Dry oil 7 | Dry oil 8 | Dry oil 9 | Dry oil 10 |
|---|---|---|---|---|---|---|---|---|---|---|
| Dub IPP ester constituting the framework of the anhydrous formulation | 35.00% | 35.00% | 35.00% | 35.00% | 35.00% | 35.00% | 35.00% | 35.00% | 35.00% | 35.00% |
| Emollient composition A | 10.00% | 20.00% | 30.00% | — | — | — | — | — | — | — |
| Emollient composition B | 0.00% | 0.00% | 0.00% | 10.00% | 20.00% | 30.00% | — | — | — | — |
| Emollient composition C | — | — | — | — | — | — | 10.00% | 20.00% | 30.00% | — |
| Emollient composition D | 20.00% | 10.00% | 0.00% | 20.00% | 10.00% | 0.00% | 20.00% | 10.00% | 0.00% | 30.00% |

Preparation mode: The components are weighed then stirred until a homogeneous phase is obtained.

Evaluation of the Dry Oils for the Body

Stability:

The stability study of the 10 oils for the body formulated is carried out at ambient temperature (AT) of the day, at 40° C. and at 50° C. for one month by visual and olfactory evaluation of the appearance, of the colour and of the odour.

As with the analysis of the stability of the 10 oil-in-water emulsions, no modification in the appearance or in the colour or any appearance of odour were observed during the visual and olfactory evaluation of the 10 dry oils formulated.

Sensory Analysis:

The 10 dry oils for the body obtained are also evaluated in sensory analysis. The evaluation criteria are then adapted to the galenics and are as follows:

Bulk intrinsic odour: odour given until a homogeneous phase is obtained by the dry oil when the bottle is open (no application carried out)

Distribution on the skin: a drop is left on the skin for 30 seconds. After 30 seconds, the capacity of the drop to be distributed or spread without manual assistance is evaluated.

Brilliance on the skin: once the dry oil is applied, does a brilliant film persist on the skin.

Fatty: (criterion evaluated on the skin 1 minute after spreading) when the skin is placed between the thumb and the index, and a friction movement is carried out, is there any resistance. Does the dry oil facilitate the displacement of the two fingers while still giving the skin an oily appearance.

Penetration: (criterion evaluated on the skin 2 minutes after spreading) by carrying out a sliding on the skin, did the dry oil disappear and no residue was recovered.

Persistent odour on the skin: (criterion evaluated on the skin 2 minutes after spreading) After 2 minutes of application, can a lingering odour be perceived on the skin.

As for the sensory analysis of the pure emollient compositions and of the formulation as O/W emulsion, a scoring system (from 0 to 5 from the least pronounced to the most pronounced) is set up in order to facilitate the operation.

Table 7 includes the average scoring results for each one of the sensory criteria evaluated for the various dry oils for the body.

TABLE 7

|  | Dry oil 1 | Dry oil 2 | Dry oil 3 | Dry oil 4 | Dry oil 5 | Dry oil 6 | Dry oil 7 | Dry oil 8 | Dry oil 9 | Dry oil 10 |
|---|---|---|---|---|---|---|---|---|---|---|
| mass intrinsic odour | 0.6 | 1.2 | 0.9 | 0.5 | 0.8 | 1.2 | 1.5 | 2 | 1.8 | 1.6 |
| distribution on the skin | 2.3 | 2.2 | 2.1 | 2.3 | 2.1 | 1.9 | 2.6 | 2.2 | 2.2 | 2.5 |
| brilliance on the skin | 2.6 | 2.1 | 2.2 | 2.2 | 2.5 | 2.3 | 2 | 1.9 | 2.4 | 1.8 |
| fat | 2.4 | 2 | 2.5 | 2.7 | 3 | 2.5 | 2.9 | 2.4 | 3.1 | 2.3 |
| penetration | 2.7 | 3 | 2.9 | 2.8 | 2.7 | 2.8 | 2.4 | 2.4 | 2.4 | 3.1 |
| lingering odour | 0.5 | 0.3 | 0.4 | 0.3 | 0.5 | 0.7 | 0.8 | 0.9 | 1.3 | 1 |

It is observed that all of the dry oils comprising the emollient compositions A, B and C have a brilliance on the skin that is more pronounced than the dry oil 10 which comprises the comparative emollient composition D. The dry oils 1 to 8 also have a lingering odour and an intrinsic odour that is less substantial than the comparative dry oil 10.

Generally, it is observed that the emollient compositions A, B and C have very close sensory profiles whether as a galenic anhydride of the dry oil type or as O/W type emulsions. These sensory profiles are moreover superior to the sensory profiles of the commercial comparative products.

The invention claimed is:

1. An emollient composition comprising at least one hydrocarbon oil in a quantity of 50 to 100% by weight with respect to the total weight of the composition, said hydrocarbon oil having an isoparaffin content by weight of 90 to 100%, a normal paraffin content by weight of 0 to 10% and having a content of carbon of biological origin greater than or equal to 90% with respect to the total weight of hydrocarbon oil, wherein the hydrocarbon oil has a content by weight of aromatic compounds less than or equal to 100 ppm with respect to the total weight of hydrocarbon oil, and wherein the hydrocarbon oil is obtained by a catalytic hydrogenation method at a temperature from 80 to 180° C. and at a pressure from 50 to 160 bars of a deoxygenated and/or isomerised feed of biological origin.

2. The emollient composition according to claim 1, wherein the hydrocarbon oil has a content of carbon of biological origin greater than or equal to 95%.

3. The emollient composition as claimed in claim 1, wherein the hydrocarbon oil has an isoparaffin content by weight of 95 to 100% with respect to the total weight of hydrocarbon oil.

4. The emollient composition as claimed in claim 1, wherein the hydrocarbon oil is chosen from non-cyclical isoparaffins comprising from 14 to 18 carbon atoms.

5. The emollient composition according to claim 1, wherein the hydrocarbon oil has a content by weight of normal paraffins less than or equal to 5% with respect to the total weight of hydrocarbon oil.

6. The emollient composition as claimed in claim 1, wherein the hydrocarbon oil comprises a content by weight of naphthenic compounds less than or equal to 1% with respect to the total weight of hydrocarbon oil.

7. The emollient composition as claimed in claim 1, wherein the hydrocarbon oil has a boiling temperature of 230 to 340° C., according to the standard ASTM D86.

8. The emollient composition as claimed in claim 1, wherein the hydrocarbon oil has a biodegradability at 28 days of at least 60% measured according to standard OECD 306.

9. The emollient composition as claimed in claim 1, wherein the hydrocarbon oil has a flash point greater than or equal to 110° C. according to the standard ASTM D93.

10. The emollient composition as claimed in claim 1, wherein the hydrocarbon oil has a vapour pressure at 20° C. less than or equal to 0.01kPa.

11. A cosmetic, dermatological or pharmaceutical composition comprising at least one emollient composition according to claim 1.

12. The cosmetic, dermatological or pharmaceutical composition according to claim 11, comprising at least one fatty body chosen from: plant oils, hydrocarbon oils other than the hydrocarbon oil of said emollient composition, plant butters, the fatty ethers and alcohols, oily esters, alkanes and silicone oils and/or at least one additive.

13. The cosmetic, dermatological or pharmaceutical composition according to claim 11, which is an anhydrous composition, an emulsion, or a dispersion.

14. The emollient composition according to claim 1, which is suitable for a topical application.

15. The emollient composition according claim 1, which is suitable for a pharmaceutical use.

16. The emollient composition according to claim 1, which is suitable for the formulation of cosmetic products, of dermatological products or of pharmaceutical products.

17. A method of cosmetic treatment of the skin comprising at least one step of application of the emollient composition according to claim 1.

18. The emollient composition according to claim 1, further comprising a colouring agent.

19. The emollient composition according to claim 1, further comprising a polymer selected from a hydrophilic or lipophilic polymers, anionic, non-ionic, cationic or amphoteric polymers, thickening polymers, gelling polymers, or dispersing polymers.

20. The cosmetic, dermatological or pharmaceutical composition according to claim 12, wherein the additive is a colouring material.

21. The cosmetic, dermatological or pharmaceutical composition according to claim 12, wherein the additive is a polymer selected from hydrophilic or lipophilic polymers, anionic, non-ionic, cationic or amphoteric polymers, thickening polymers, gelling polymers, or dispersing polymers.

* * * * *